United States Patent [19]

Copelan

[11] Patent Number: 4,830,854
[45] Date of Patent: May 16, 1989

[54] CHEMICAL SPLINTER REMOVAL

[75] Inventor: Russell I. Copelan, Colorado Springs, Colo.

[73] Assignee: James B. Copelan, Glendale, Calif.

[21] Appl. No.: 134,993

[22] Filed: Dec. 18, 1987

[51] Int. Cl.[4] .............................................. A61K 9/00
[52] U.S. Cl. ..................................... 424/445; 424/446
[58] Field of Search ................................ 424/443–447

[56] References Cited

U.S. PATENT DOCUMENTS

| | | | |
|---|---|---|---|
| 2,451,994 | 10/1948 | Towns | 128/354 |
| 2,602,042 | 7/1952 | Abbott | 167/84 |
| 3,208,908 | 9/1965 | Maxwell et al. | 167/73 |
| 3,281,331 | 10/1966 | Bergkvist | 195/66 |
| 3,409,719 | 11/1968 | Noe et al. | 424/94 |
| 3,731,683 | 5/1973 | Zaffaroni . | |
| 4,078,564 | 3/1978 | Spina et al. | 424/94 |
| 4,122,158 | 10/1978 | Schmitt | 424/94 |
| 4,576,817 | 3/1986 | Montgomery et al. | 424/94 |

OTHER PUBLICATIONS

M. Davies and R. Marks, Br. J. Dermatol. 95: 187–192 (1976).
R. Marks, M. Davies, A. Cattel, J. Invest Dermatol 64: 283 (1975).
C. Huber and E. Christophers, Arch. Derm. Res. 257, 294–297 (1977).
C. F. Vickers, in Dermatology in General Medicince. (T. B. Fitzpatrick, A. Z. Eisen, K. Wolf, I. M. Freedberg, K. F. Austen, eds.) pp. 2545–2549 (New York: 1987).
E. G. Weirich, J. K. Longauer, and A. H. Kirkwood, Dermatologica. 152:87–99 (1976).
H. P. Baden, J. Invest Dermatol. 61:330 (1977).

Primary Examiner—Nancy A. B. Swisher
Attorney, Agent, or Firm—Linda F. Gould

[57] ABSTRACT

A method is provided of facilitating the removal of foreign objects embedded in skin, generally referred to as splinters, by chemical means. The method involves topically applying, to the skin at a point adjacent to the splinter, such as the point at which the splinter entered the skin, a chemical composition including salicylic acid. The chemical composition may also include an antibiotic to promote healing, and a vehicle, such as petrolatum. When placed in contact with the skin at a point adjacent to the splinter, by a dressing or other carrier secured to the skin, the chemical composition causes desquamation of injured skin scales, epidermal hydration, and diffuse loosening of the embedded splinter.

15 Claims, 4 Drawing Sheets

CHEMICAL SPLINTER REMOVAL

1.0 BACKGROUND OF THE INVENTION

1.1 Technical Field

This invention pertains to the chemical removal of foreign material embedded in skin, generally referred to as a splinter. Such splinter removal involves the use of various pharmaceutical compositions useful in chemically removing the splinter from the skin, a method of using those chemical compositions for this purpose, and a bandage which includes the chemical composition to facilitate removal of a splinter.

1.2 Background Art

When foreign material becomes embedded in the epidermis, and in particular in the stratum corneum layer of the skin, that foreign material may be referred to as a splinter. The splinter causes injury to skin cells and pain, both upon entry and while the splinter remains embedded in the skin.

Commonly, splinters are removed by a mechanical tool, such as tweezers or a needle. One such device is shown in U.S. Pat. No. 2,451,994 to Towns. A splinter remover involving a pair of tweezers, with a reservoir for antiseptic, is described. The splinter remover allows the mechanical removal of a splinter, with the application of antiseptic by the same device.

The splinter removal methods known in the prior art all involve a significant detrimental effect: they are painful. Mechanical tools such as tweezers and needles, even when skillfully used, result in injury to surrounding skin cells in the stratum corneum layer of the skin, and activate pain sensations.

Removal of splinters by chemical means is not taught in the prior art. Various chemicals have been used to dissolve necrotic tissue caused by burning and to hasten the healing of burns. Application of such a chemical debriding agent is frequently accomplished by a bandage or other topical dressing. For example, U.S. Pat. No. 4,122,158 to Schmitt discloses a method of topically applying an antibacterial, antibiotic, antifungal or proteolytic agent in a polymer of a particular formula. Application of such an "agent-loaded" polymer to a burned surface by means of an absorbent carrier is described.

Similarly, U.S. Pat. No. 3,281,331 to Beggkvist teaches the use of a proteolytic enzyme for the treatment of wounds and debriding of third degree burns. Combining a proteolytic enzyme with an antibiotic in an ointment base and application by means of a bandage carrier is described.

U.S. Pat. No. 3,409,719 to Noe and Beckhorn discusses the use of a bacterial enzyme produced by the growth of *Bacillus subtilis* for the debridement of necrotic tissue. The enzyme may be prepared in ointment form for topical application.

An enzymatic composition comprising fibrinolysin and desoxyribonuclease, together with an antibiotic, is described as a debriding agent in U.S. Pat. 3,208,908 to Maxwell and Loomis. However, these patents do not teach the use of such debriding agents for the removal of foreign objects embedded in skin.

Removal of splinters through chemical debridement is most efficiently accomplished by incorporating the active chemical accomplishing the debridement into a bandage for application to the skin. U.S. Pat. No. 3,731,683 to Zaffaroni discloses a bandage design to allow the administration of controlled therapeutically effective quantities of topically active drugs. Among the drugs mentioned is salicylic acid. However, the patent emphasizes the unique controlled release rate of the bandage, and does not contemplate a particular use for the bandage with any particular chemical.

Other medicated bandages are known in the prior art for use in treating various skin disorders. U.S. Pat. No. 4,576,817 to Montgomery and Pellico discloses a bandage or pad incorporating an enzymatic material to inhibit bacterial growth. U.S. Pat. No. 2,602,042 to Abbott describes the preparation of a medical dressing incorporating a medication, such as an antibiotic substance, for treatment of burns or wounds.

Although the inventions described in these prior patents are effective for their intended purpose, none establishes a chemical method for the removal of splinters. The various chemical debriding agents and medicated bandages described above are designed to hasten healing after a severe burn or other wound is incurred. Polymers and enzymes, sometimes in conjunction with antibiotics, are used to dissolve necrotic tissue resulting from the catastrophe or burn. Any resulting desquamation effected by these chemicals and bandages involved only necrotic skin cells, and did not purport to effect any foreign material in the skin. Although these methods of treatment are analogous to the invention disclosed herein, none of these previous methods accomplishes the removal of splinters.

The mechanical method of splinter removal described in the Towns patent is effective for splinters close enough to the surface of the skin to be grasped with tweezers. However, this method can be quite painful, as well as injurious to viable skin cells.

Use of salicylic acid as a keratolytic agent is known in the prior art, for treatment of skin disorders other than splinter removal. Medical use of salicylic acid in dermatological cases is based on its action of solubilizing the intercellular cement that binds scales in the stratum corneum while increasing water binding, and thus hydrating the keratin. Although these chemical properties of salicylic acid have been reported in M. Davies and R. Marks, Br. J. Dermatol. 95: 187–192 (1976), R. Marks, M. Davies and A. Cattel, J. Invest. Dermatol. 64: 283 (1975), and C. Huber and E. Christophers, Arch. Derm. Res. 257, 294–97 (1977), these references do not explore the possible use of salicylic acid as a splinter removal agent.

The invention disclosed herein uses features of salicylic acid in particular medical compositions, in a manner not revealed in the prior art. The object of this invention is to provide a painless, effective method of removing splinters.

2. DISCLOSURE OF THE INVENTION

2.1 Summary of the Invention

The chemical splinter removal of this invention comprises a method, utilizing chemical compositions, for removing foreign objects embedded in skin.

More specifically, this invention involves the topical application of salicylic acid ($o$-$HOC_6H_4COOH$), in combination with a variety of other chemicals, to skin at the site of splinter entry.

Compositions to be used in this method of splinter removal utilize varying strengths of salicylic acid. In some cases, crystalline salicylic acid will be dissolved in an organic solvent, which may be adsorbed onto an adhesive surface. Suitable solvents include synthetic cellulose derivatives and polyhydroxy compounds.

Salicylic acid can also be formulated into a variety of pharmaceutical forms such as ointments and films. A water-in-oil type ointment base containing emollient hydroxy carbons such as petrolatum has been found to be a desirable vehicle.

A selected antibiotic may be added to the salicylic acid mixture. Typical antibiotics which may be included in the composition are broad spectrum topical antibiotics such as gramicidin and zinc bacitracin. Other antibiotics may be used as well.

The resulting mixture can be applied to the kin at a location adjacent to the splinter. Application may be accomplished by placing the ointment based mixture on a piece of gauze or other bandage material, and taping or other wise securing the bandage material to the splinter entry point. The solvent based mixture may be advantageously adsorbed onto hypoallergenic adhesive surfaces, and placed on the injured skin in this fashion.

Additional advantages of this invention will become apparent from the description which follows, taken in conjunction with the accompanying drawings.

2.2 Brief Description of the Drawings

2.3 Detailed Description of the Preferred Embodiment

Figure 4:
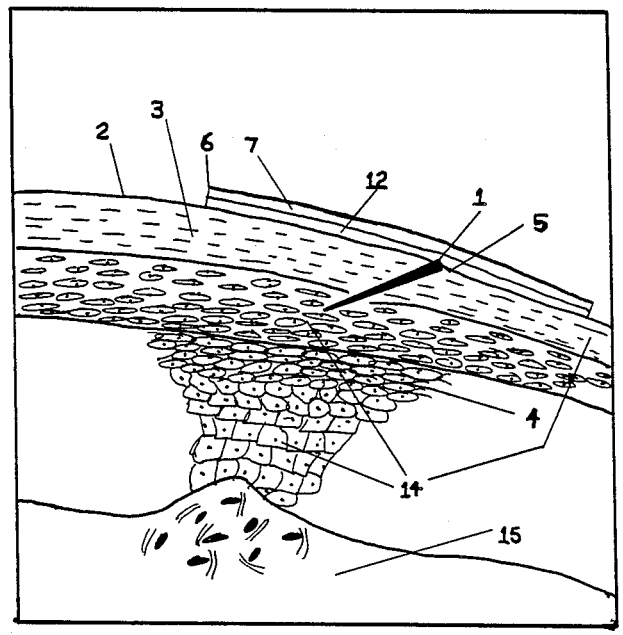
FIG. 4 is a view of a splinter embedded in skin, showing the application of a bandage-type carrier incorporating a composition including salicylic acid.

The features of the splinter removal technique according to the present invention can be better understood by reference to FIG. 4. As is shown in FIG. 4, a splinter 1 is embedded into the skin 2 of a finger of a human individual, for example. In order to remove the splinter in accordance with the present invention, a chemical composition (not shown) which is adsorbed onto an adhesive surface 12 of a bandage 6 is applied to the skin at a point 5 adjoining the splinter 1. The point 5 will generally be at the point of entry of the splinter into the skin 2. After the chemical composition has been in contact with the skin for a predetermined amount of time, desquamation occurs resulting in non-viable skin cells 4 around the splinter 1 peeling off, allowing the splinter 1 to be removed with those non-viable skin cells 4.

Figure 3:
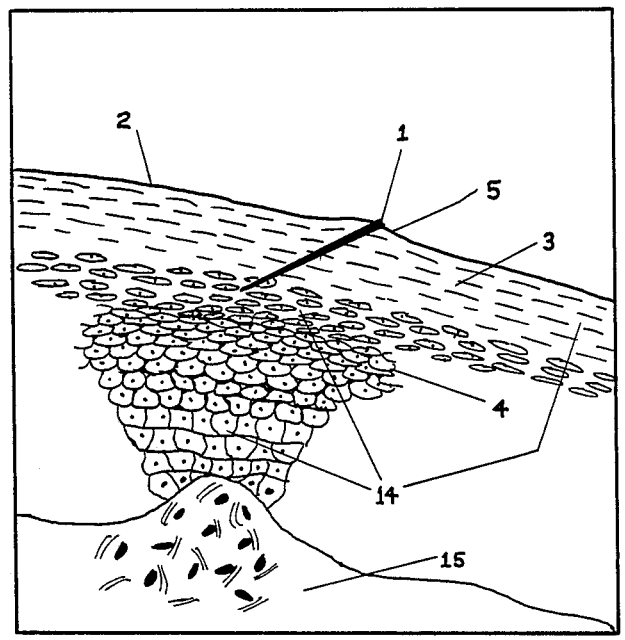
FIG. 3 is a view of a splinter embedded in the stratum corneum, or horny layer, of skin.

As shown in FIG. 3, when a foreign object such as a splinter 1 enters the stratum corneum 3, or horny layer, of skin 2, the splinter may cause cell rupture, hemorrhage, bacterial contamination, tissue swelling, and activation of pain sensations. The epidermis 14 consists of multiple layers, including the most superficial layer known as the stratum corneum 3. The dermis 15 lies beneath the epidermis 14. Skin cells 4 of the epidermis 14 surrounding the splinter 1 are thinned and stretched, so as to inhibit easy extraction by any mechanical means.

The chemical composition utilized in this splinter removal technique comprises varying strengths of salicylic acid, in combination with a non-aqueous solvent or ointment base. The salicylic acid composition promotes hydration and selective removal of damaged superficial skin cells. This desquamation results in the splinter being freed from the injured skin cells, which otherwise impede removal of the splinter, without toxicity to surrounding, viable skin.

FIG. 4 reveals the application of the salicylic acid composition to the skin 2 by means of a bandage 6. The bandage 6 is applied to a point adjacent to the splinter 5 so as to topically apply the salicylic acid composition adsorbed onto the adhesive surface 12 of the bandage 6 for twenty-four to forty-eight hours. The extent of entry of the composition adsorbed onto the adhesive surface 12 is determined by a number of factors including the form of the composition adsorbed onto the adhesive surface 12, the integrity of the skin 2, skin hydration, and the type of occlusive dressing 7.

Figure 5:
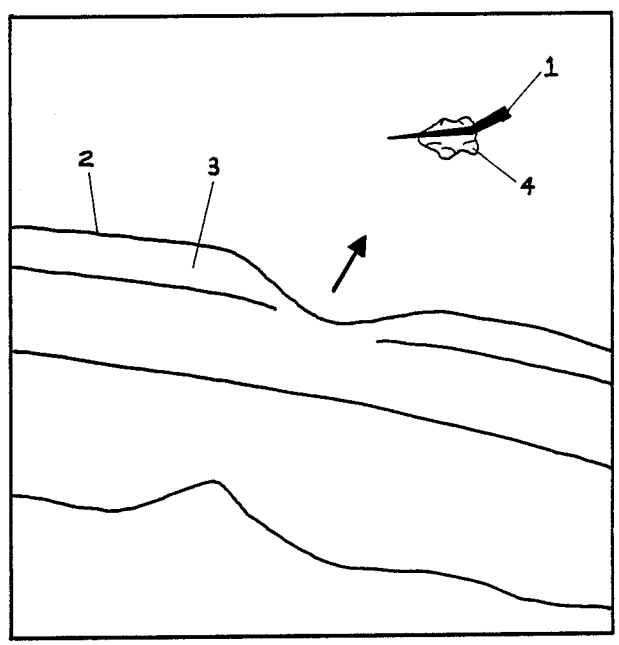
FIG. 5 is a view of a splinter, together with necrotic skin scales, being removed from skin, using the technique described herein.

During the application of the salicylic acid composition, desquamation of the stratum corneum 3 occurs, causing non-viable skin cells to peel off, with little to no effect on viable epidermis 14. FIG. 5 demonstrates the desired and ultimate result of the completed process. The splinter 1, together with skin cells 4 injured by the entry of the splinter 1, are debrided from the skin 2 by the action of the salicylic acid composition.

Figure 1:
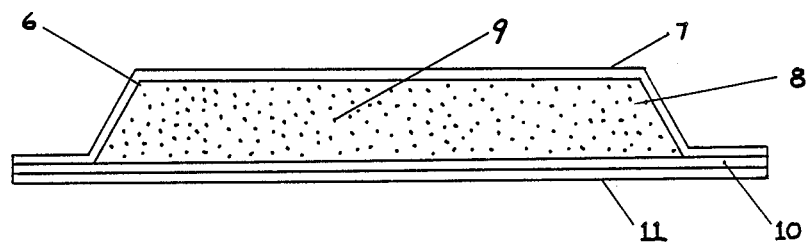
FIG. 1 is a cross-sectional vie of a bandage which can be utilized in the splinter removal process for application of a composition including salicylic acid.

A composition including salicylic acid may be applied to the skin by means of a bandage 6 or other carrier as shown in FIG. 4. FIG. 1 shows a possible configuration for the bandage 6. A backing layer 7, impermeable to keratolytic decomposition, forms the outside boundary of the bandage 6. A reservoir 8 of the active salicylic acid composition is contained by the backing layer 7. The reservoir 8 may consist of woven filaments 9 impregnated with a composition including salicylic acid in an ointment blend. This bandage 6 is applied to the skin by means of an adhesive 10. Prior to application, a protective peel strip 11 covers the adhesive 10 and reservoir 8.

Figure 2:
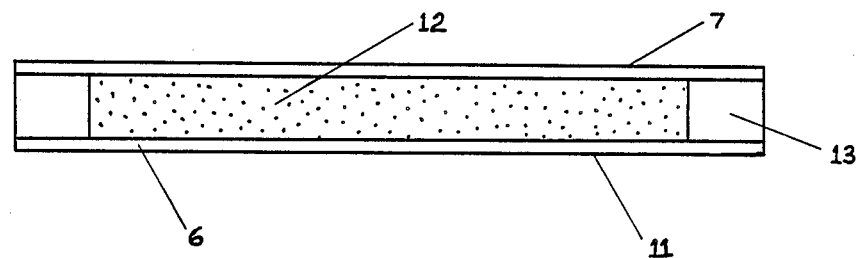
FIG. 2 is a bottom view of a bandage which can be utilized in the splinter removal process for application of a composition including salicylic acid.

FIG. 2 reveals another possible configuration of a bandage 6 for the application of the salicylic acid composition. As in the bandage 6 shown in FIG. 1, a backing layer 7 encompasses the salicylic acid composition. In this case, however, the salicylic acid composition is adsorbed onto an adhesive surface 12 in a manner which does not cover the ends of the adhesive surface 13, and with no specially constructed filament-based reservoir. A protective peel strip 11 covers the adhesive surface 12 until the bandage 6 is applied to the skin 2.

Other forms of application of the salicylic acid composition, not revealed in the drawings, are possible. The drawings disclose only some of the possible embodiments of the invention. Typical of a useful application bandage would be a laminate of: a backing member defining one face surface of the bandage, an adhesive, possibly hypo-allergenic or otherwise desirable for contact with skin, the external surface of said pressure sensitive adhesive defining the other face surface of the bandage, and some type of pharmaceutical delivery form consisting of the salicylic acid composition.

The following example will serve to illustrate the invention without in any way being limiting thereon.

2.4 Example

An embodiment of this invention may be prepared by mixing salicylic acid in white petrolatum, in a ratio of 40% acid to petrolatum. The resulting petrolatum based mixture may be topically applied to the splinter site, utilizing an occlusive dressing.

In a study utilizing a composition corresponding to the above example, there was moderately marked loosening of a splinter embedded in the stratum corneum, within 36 hours of applying the salicylic acid composition. There was no discernible erythema of the site where the composition was applied. Hydration of that site was indicated by moderate to marked, homogeneous diffuse fading. As a result, pain caused by entry of the splinter was relieved, without irritation or increased pain as would result from mechanical removal of the splinter.

The invention has been described in detail with particular reference to preferred embodiments thereof. As will be apparent to those skilled in the art in the light of the accompanying disclosure, many alterations, substitutions, modifications, and variations are possible in the practice of the invention without departing from the spirit and scope of the invention.

I claim:

1. A splinter removal agent comprising, in combination, an effective amount of salicylic acid in a non-aqueous solvent.

2. A splinter removal agent as described in claim 1, including, in combination, an antibiotic.

3. A splinter removal agent as described in claim 1, wherein the removal agent is adsorbed onto an adhesive surface.

4. A splinter removal agent comprising, in combination, an effective amount of salicylic acid, mixed in an ointment base.

5. A splinter removal agent as described in claim 4, wherein the ointment base is white petrolatum.

6. A splinter removal agent as described in claim 4, including, in combination, an antibiotic.

7. A splinter removal agent as described in claim 4, wherein the composition is placed in an occlusive dressing.

8. A method for facilitating the removal of a splinter embedded in the skin, comprising the steps of:

forming a chemical composition comprising salicylic acid in combination with a non-aqueous solvent, and applying the chemical composition to the skin at a location adjoining the splinter.

9. A method as defined in claim 8 further comprising:

including an antibiotic with the chemical composition.

10. A method as defined in claim 8 wherein:

the chemical composition is applied to the skin by adsorbing the chemical composition onto an adhesive surface, and applying the adhesive surface to the skin at a location adjoining the splinter.

11. A method as defined in claim 8 wherein:

the non-aqueous solvent comprises an ointment base.

12. A method as defined in claim 8 further comprising:

leaving the chemical composition on the skin for a predetermined sufficient amount of time for desquamation of skin cells in the stratum corneum layer of the skin to occur.

13. A method as defined in claim 12 further comprising:

removing the splinter and adjoining nonviable skin cells.

14. A splinter removal bandage for topical application to the skin, comprising:

a chemical composition comprising an effective amount of salicylic acid;

a reservoir of woven filaments impregnated with said composition; and an adhesive connected to the reservoir for holding the woven filaments impregnated with the chemical composition in contact with the skin at a location adjoining the splinter.

15. A splinter removal bandage for topical application to the skin, comprising:

a chemical composition comprising an effective amount of salicylic acid; and an adhesive onto which the chemical composition is adsorbed for holding the chemical composition in contact with the skin at a location adjoining the splinter.

* * * * *